United States Patent [19]
Nyberg et al.

[11] Patent Number: 4,941,134
[45] Date of Patent: Jul. 10, 1990

[54] SONIC GENERATOR

[75] Inventors: Christopher A. Nyberg, North Vancouver; James G. Jackson, Burnaby; Jan Brdicko, West Vancouver, all of Canada

[73] Assignee: Arc Sonics Inc., British Columbia, Canada

[21] Appl. No.: 176,716

[22] Filed: Apr. 1, 1988

[51] Int. Cl.⁵ .............................................. H04R 1/02
[52] U.S. Cl. .................................... 367/142; 366/108; 367/176
[58] Field of Search ................. 181/113, 142; 367/142, 367/148, 156, 168, 174, 175, 176; 310/26, 80, 81, 84, 103–105, 109, 111, 112; 166/72; 175/53, 55; 366/108, 116, 124, 127, 600

[56] References Cited
U.S. PATENT DOCUMENTS

| | | | |
|---|---|---|---|
| 2,152,728 | 8/1985 | Bodine . | |
| 2,468,515 | 4/1949 | Robinson | 310/29 |
| 2,567,527 | 9/1951 | Parks | 286/26 |
| 2,907,347 | 10/1959 | Parks | 137/620 |
| 2,960,317 | 11/1960 | Bodine, Jr. | 366/600 X |
| 3,153,530 | 10/1964 | Bodine | 366/600 X |
| 3,167,669 | 1/1965 | Bodine | 175/55 |
| 3,189,536 | 6/1965 | Bodine | 175/55 |
| 3,360,056 | 12/2967 | Bodine | 175/55 |
| 3,633,877 | 1/1972 | Bodine | 259/72 |
| 3,684,037 | 8/1972 | Bodine | 175/56 |
| 3,848,672 | 11/1974 | Bodine | 166/249 |
| 3,941,552 | 3/1976 | Cottell | 431/2 |
| 4,252,189 | 2/1981 | Bodine | 60/249 |
| 4,265,129 | 5/1981 | Bodine | 166/249 |
| 4,323,119 | 4/1982 | Bodine | 74/61 |
| 4,342,364 | 8/1982 | Bodine | 166/177 |
| 4,377,391 | 3/1983 | Cottell | 74/51 |
| 4,728,837 | 3/1988 | Bhadra | 310/81 |
| 4,780,861 | 10/1988 | Stembridge et al. | 367/176 X |
| 4,821,244 | 4/1989 | Wood | 367/159 |

Primary Examiner—Brian S. Steinberger
Attorney, Agent, or Firm—John Russell Uren

[57] ABSTRACT

A sonic generator comprises a resonant bar, a housing and magnetic excitation units connected between the resonant bar and the housing. The magnetic excitation units are connected to the bar using a mounting connection which is a sleeve having an inside diameter slightly greater than the outside diameter of the bar. A resilient elastomer such as urethane is mounted between the sleeve and the resonant member.

7 Claims, 5 Drawing Sheets

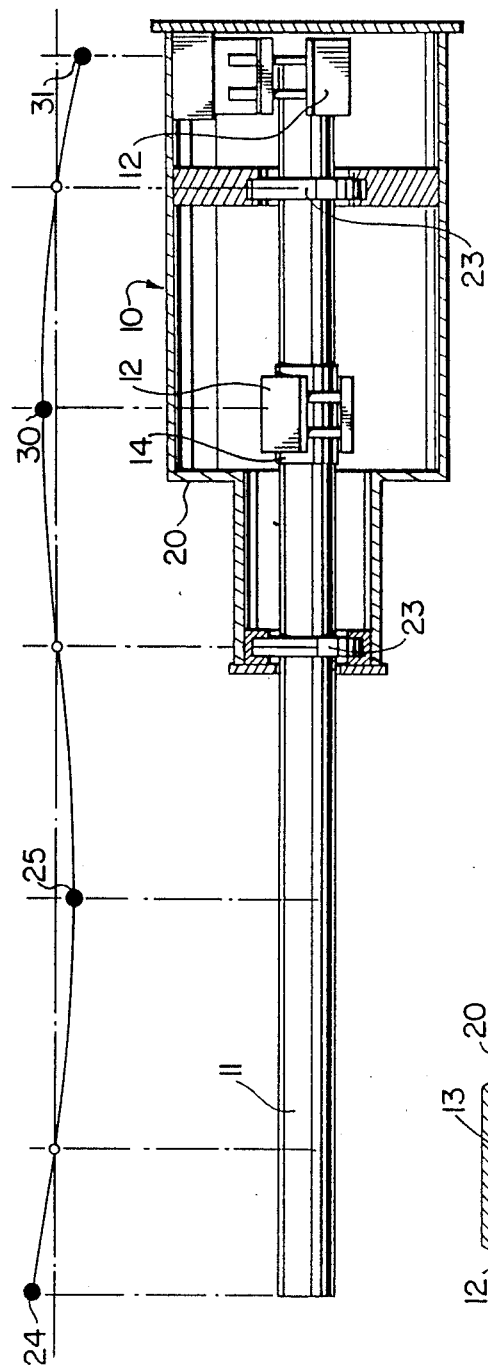
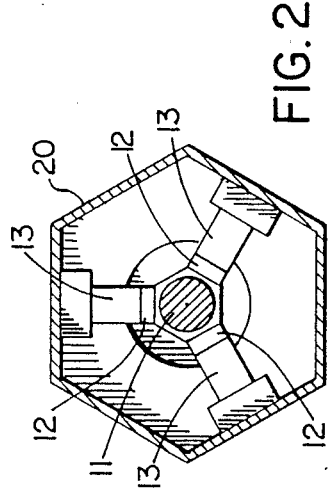
FIG. 1
FIG. 2

SONIC GENERATOR

INTRODUCTION

This invention relates to a sonic generator and, more particularly, to a sonic agitator for the transmission of energy into fluid mediums.

BACKGROUND OF THE INVENTION

Sonic generators used to convert electrical energy into acoustic and kinetic energy for transmission to fluid mediums are known. Such devices are illustrated, for example, in U.K. Patent Specification 2,152,728 to Bodine and U.S. Pat. No. 2,468,515 to Robinson.

The sonic generators there disclosed, however, suffer disadvantages. The apparatus taught by Bodine in the aforementioned U.K. patent utilizes orboresonant drives similar to the types described in Bodine's U.S. Pat. Nos. 3,633,877, 3,684,037, 3,360,056 and 4,265,129. These drives limit the upper range of frequencies such units can transmit to a fluid medium. Since the transmission of acoustic power between the resonant bar and the fluid is less efficient at lower frequencies, this limitation lowers the acoustic efficiency of the Bodine apparatus. Further, Bodine necessarily utilizes a coupling between this orbiting mass oscillators and his resonant bar which attempts to isolate the inertial forces of the vibrating bar from the motor. Without such coupling, the magnitude of these forces are sufficient to cause relatively rapid failure of the orbiting mass oscillator drive motors, be they hydraulic or electric. Bodine further exposes a large force on a relatively small member used to support the resonant bar with the result, again, that failure of the apparatus is increased. Because of the high forces imposed upon the motors and the insufficient support provided in the Bodine design, premature failure of the unit is likely.

U.S. Pat. No. 2,468,515 to Robinson teaches restraining a resonating bar with steel bushings at respectively oppositely located end portions of the bar. Such supports cause energy to be lost through the support structure which energy would be better utilized in the fluid medium. Further and because of the mounting, Robinson's structure has a very high stress concentration both at the support point and at the point of maximum bending stress. Such stress concentration can eventually cause unnecessary damage to the resonant member and/or premature failure and limit the mechanical stresses that can be sustained without failure. Yet a further disadvantage of the Robinson apparatus is that he utilizes a two dimensional movement of his resonant bar. Such a design causes the pressure to radiate outwardly into the fluid medium in a single plane whereas with a three dimensional movement of the resonant bar, pressure will radiate outwardly from the bar in all directions.

SUMMARY OF THE INVENTION

According to the invention, there is disclosed a sonic generator comprising a resonant member having a plurality of nodes and anti-nodes, resilient mounting and locating means located between a housing and said resonant member, electromagnetic drive means coupled to said resonant member with mounting means, said mounting means comprising an outer sleeve surrounding said resonant member and a resilient elastomeric material between said outer sleeve and said resonant member.

BRIEF DESCRIPTION OF THE SEVERAL VIEWS OF THE DRAWINGS

A specific embodiment of the invention will now be described, by way of example only, with the use of drawings in which:

FIG. 1 is a diagrammatic front view of the sonic generator according to the invention also illustrating the second mode shape of the generator;

FIG. 2 is an end view of the sonic generator of FIG. 1;

DESCRIPTION OF SPECIFIC EMBODIMENT

Figure 3:
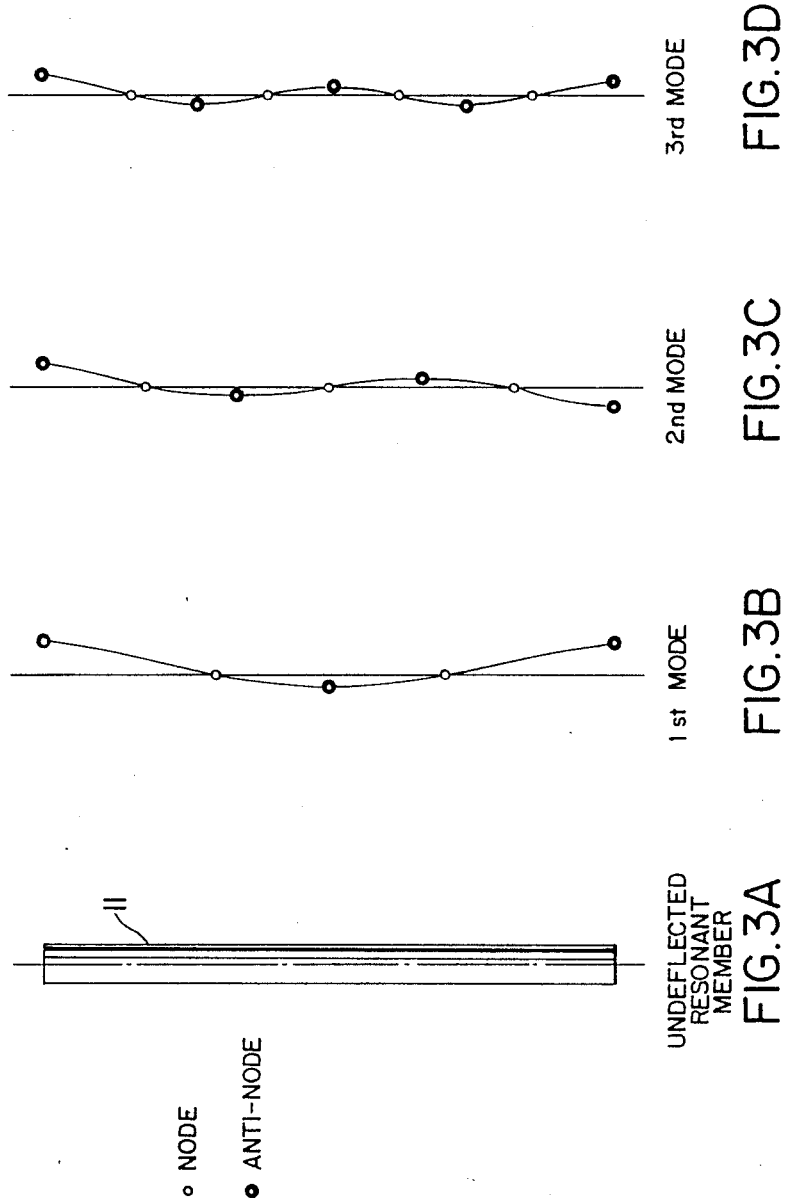
FIGS. 3A-3D diagrammatically illustrate the resonant member in its various characteristic mode shapes.
Figure 4:
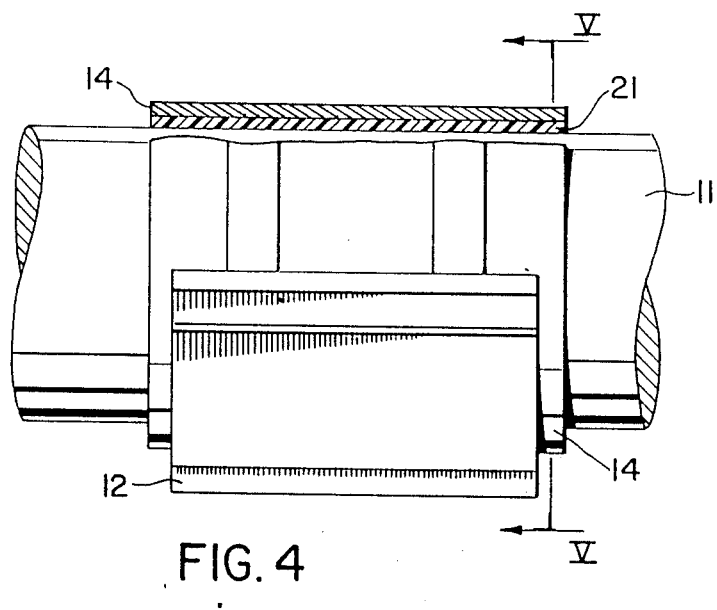
FIG. 4 is an enlarged front view of the motor mounting area of the sonic generator according to the invention.
Figure 5:
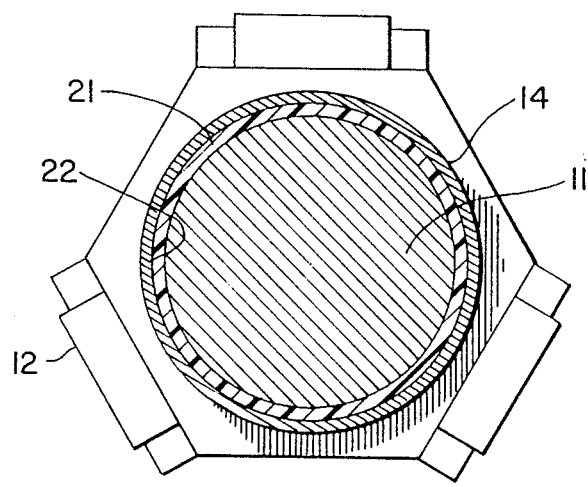
FIG. 5 is a top view of the motor mounting area of FIG. 4 taken along the plane V—V of FIG. 4.

Referring now to the drawings, a sonic generator is illustrated generally at 10 in FIG. 1. It comprises a resonant bar or tube 11 extending substantially the length of the generator 10 and being mounted, at one end, within a housing 20.

Two variable frequency electromagnetic excitation units 13, each consisting of one electromagnet per phase are energized by a three phase AC power supply (not illustrated). The armature components are rigidly mounted using a bolted, clamped or welded connection, to an excitation unit isolation sleeve 14, made from a metal, preferably steel, tube concentrically located about the resonant bar and having an inside diameter 22 slightly greater than the outside diameter of the resonant bar 11 and a length which is desirably at least as great as its diameter. The annular space between the inside of the isolation sleeve 14 and the outside diameter of the resonant bar 11 is solidly filled with a resilient elastomeric compound 21 such as urethane. The urethane further solidly bonds the sleeve 14 to the resonant bar 11.

OPERATION

Figure 6A:
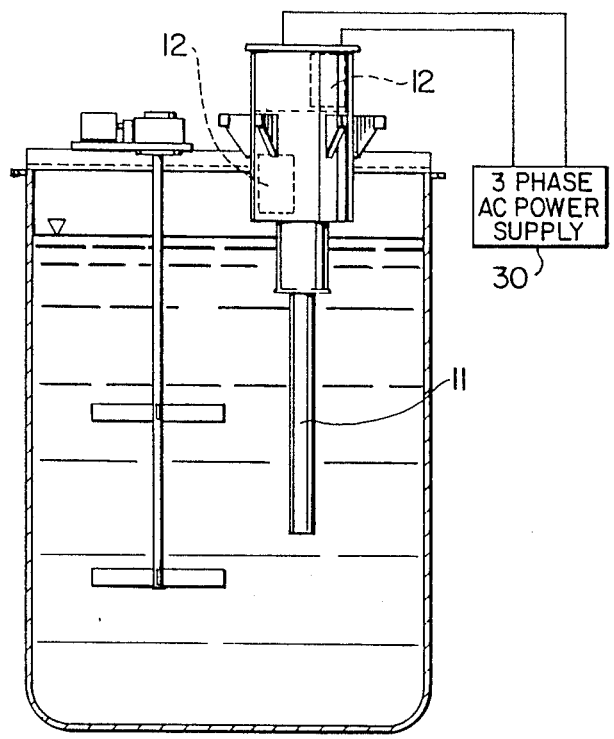
FIG. 6 illustrates the sonic generator in operating condition in an agitated tank.
Figure 6B:
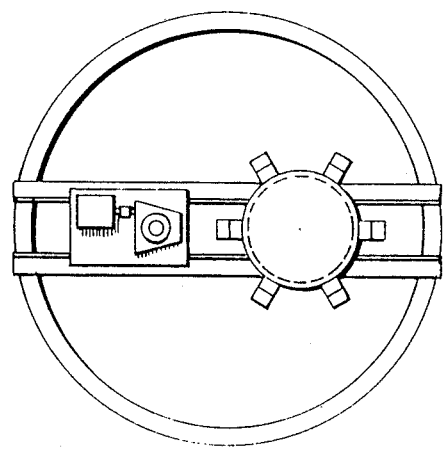

In operation, it will be assumed that the sonic generator 10 is to be mounted in a fluid medium in a manner similar to FIG. 6 for example, such that when the sonic generator 10 is operative, energy is transferred from the resonant bar 11 of the sonic generator 10 to the fluid medium.

The mode shape of the resonant member, said member comprised of the resonant bar 11, the driven components of the magnetic excitation units 12, referred to as the armatures, and the isolation sleeve 14 is known for the various natural frequencies of the system. For example and with reference to FIG. 3, the undeflected resonant bar 11 is illustrated diagrammatically in FIG. 3A and the three mode shapes for the three lowest natural frequencies of the bar are illustrated in FIGS. 3B, 3C and 3D.

To excite the resonant member, the magnetic excitation units 13 are energized at the desired natural frequency of the resonant member by a variable frequency three phase AC power supply 30 (FIG. 6A). Each phase of the power supply energizes one of three phases of the magnetic excitation units 13. Each phase of the excitation units is spaced at 120 degrees radially about the resonant member such that the force vector produced by the excitation unit rotates at a constant rate about the longitudinal axis of the resonant system at the driven frequency. This causes a three dimensional, nutational vibration of the resonant member which allows acoustic energy to propagate radially off of the resonant bar in all directions. When the member is excited at its natural frequency, an increased power transmission ability for a given excitation force is obtained.

Figure 7:
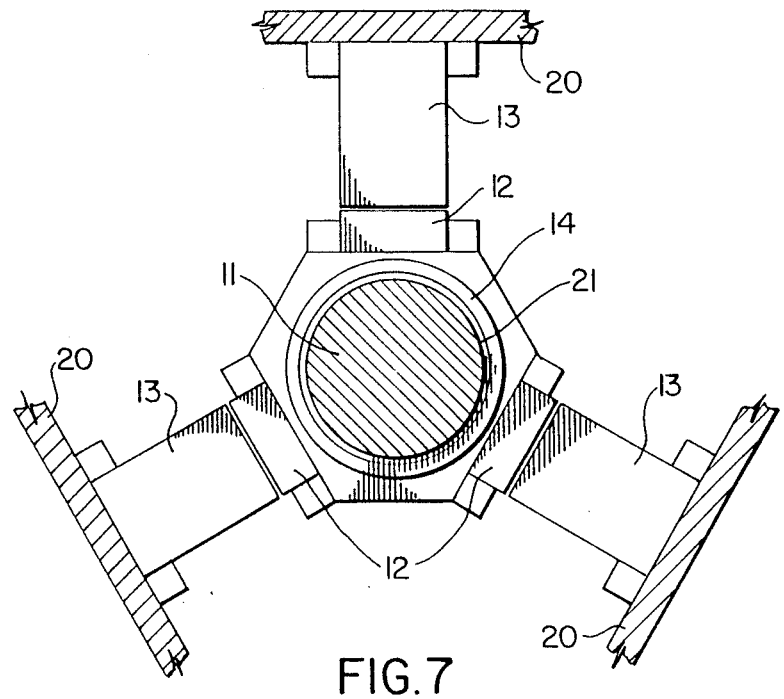
FIG. 7 is an end view of the electromagnetic excitation units and the armatures attached to the resonant bar through the mounting means.
Figure 8:
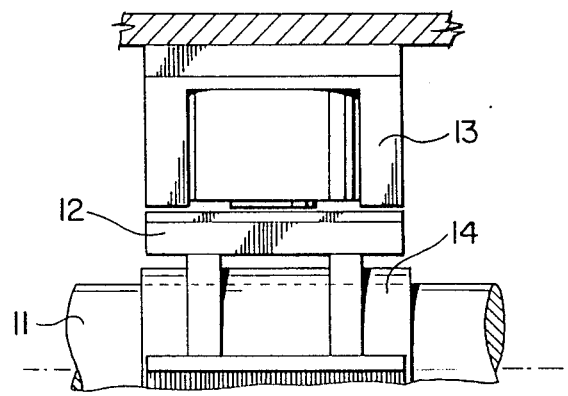
FIG. 8 is a partial side view of FIG. 7.

The resonant bar 11 is elastically mounted within the housing 20, as illustrated in FIG. 1, at the node points where there is substantially zero vibration amplitude of the resonant bar 11. It is advantageous to mount the resonant bar 11 to the housing 20 at these points since, with such a mounting, relatively little power is lost through the nodal support positioner 23 and since there is little or no movement of the resonant bar 11 at these node points when the resonant bar 11 is resonating, locating the resonant system, particularly the armatures 12, with respect to the electromagnetic excitation unit(s) 13 with the nodal support positioners 23 can be accomplished with great accuracy. FIGS. 7 and 8 illustrate the relative position of the various components.

Again as seen in FIG. 1, four (4) points of maximum amplitude are illustrated. These points, shown at 24, 25 30 and 31, are anti-nodes. Within the housing 20, the excitation unit armatures 12 are mounted to the resonant bar 11 through the isolation sleeves 14 and resilient elastomeric compound 21 at the anti-nodes. The power transmission between both the excitation unit electromagnets 13 and the armatures 12, and the resonant bar 11 and the fluid medium in which the sonic generator 10 is mounted, is most efficient at the anti-nodes, since power is transferred both to the fluid medium from the resonant bar 11, and to the resonant member from the electromagnetic excitation units 13, in a direct proportion to the amplitude of vibration of the resonant bar 11.

The use of the resilient elastomeric component and the sleeve 14 substantially reduces stress concentrations applied to the resonant bar 11 caused by rigidly mounting as by clamping or bolting or welding, the excitation unit armatures 12 directly to the bar. This is so because the free surface area of the elastomer 21 is quite small relative to the constrained surface area, which results in a layer which has very little compressibility and which, therefore, will transmit substantially all of the force between the components of the resonant member, while at the same time the elastomer allows the resonant bar 11 to freely flex in its characteristic mode shape by absorbing the small relative deflections of the bar 11 caused by the flexure inherent in the characteristic mode shape.

Similarly, while the elastomeric substance used between the resonant bar 11 and the sleeve 14 is described as being urethane, it is clear that many other substances could be used with the appropriate operating characteristics including, as described, a resilient elastomeric component.

The sonic generator has been described as being used in a fluid medium and it should be understood that such a fluid medium could be a liquid, a gas or a solid which has been fluidized by grinding to a finite particle size.

Many modifications additional to those described may readily occur to those skilled in the art to which the invention relates and the specific embodiments described above should be taken as illustrative only and not as limiting its scope as defined in accordance with the accompanying claims.

I claim:

1. A sonic generator comprising a resonant member having a plurality of nodes and anti-nodes, means located between a housing and said resonant member at at least two nodal locations of said resonant member for substantially isolating the vibration of said member from said housing, said resonant member including a resonant bar and electromagnetic drive means mounted to said resonant bar with drive mounting means, said drive mounting means comprising an outer sleeve surrounding said resonant bar and a resilient elastomeric material between said outer sleeve and said resonant bar, said resilient material having a free surface area and a constrained surface area, said free surface area of said elastomeric material being small relative to said constrained surface area so as to allow said resonant member to freely flex in the characteristic mode shape of said resonant member, said electromagnetic drive means being operable to transmit vibration to said resonant member at a frequency close to or substantially identical with a resonant frequency of said member.

2. A sonic generator as in claim 1 wherein said resonant member has an operating mode for each natural frequency of said resonant member, said operating mode having nodes and anti-nodes, said electromagnetic drive means being mounted to said drive mounting means at one of said anti-nodes.

3. A sonic generator as in claim 2 wherein said resilient elastomeric material is urethane compound.

4. A sonic generator as in claim 3 wherein said outer sleeve is metallic.

5. A sonic generator as in claim 4 wherein the number of electromagnetic drive means is two.

6. A sonic generator as in claim 2 wherein said electromagnetic drive means is activated by a three phase AC power supply.

7. A sonic generator as in claim 1 wherein said resonant member is elastically constrained at said nodal locations.

* * * * *